United States Patent [19]

Smirmaul

[11] 4,375,320
[45] Mar. 1, 1983

[54] DUAL IMAGE CORNEAL RADIUS MEASUREMENT

[76] Inventor: Heinz J. Smirmaul, 1207 Spring Lake Dr., Duncanville, Tex. 75116

[21] Appl. No.: 183,748

[22] Filed: Sep. 5, 1980

[51] Int. Cl.³ .............................................. A61B 3/10
[52] U.S. Cl. .................................... 351/212; 351/221
[58] Field of Search ................ 351/6, 13, 16; 350/35, 350/36

[56] References Cited

U.S. PATENT DOCUMENTS

| | | | |
|---|---|---|---|
| 4,046,463 | 9/1977 | La Russa et al. | 351/13 |
| 4,157,859 | 6/1979 | Terry | 350/35 |
| 4,165,744 | 8/1979 | Cravy et al. | 128/303.1 |

Primary Examiner—F. L. Evans

Attorney, Agent, or Firm—Richards, Harris & Medlock

[57] ABSTRACT

An instrument with a microscope brings into focus the cornea of a patient's eye for measurement of the radius of curvature of the cornea. Included is a pair of parallel spaced apart linear objects in a plane perpendicular to the optical axis of the eye and of the microscope. A square rod of refractile transparent material is mounted in the field of view of the microscope with a diagonal of the cross-section thereof common to the optical axis of the microscope. Structure is provided for rotating the rod around the optical axis of the microscope to produce a parallel line offset-overlap pattern of the objects as viewed through the rod. Structure is further provided for measuring the angle between a perpendicular from the long axes of the objects, and the orientation of the rod at which the pattern is produced.

8 Claims, 11 Drawing Figures

DUAL IMAGE CORNEAL RADIUS MEASUREMENT

TECHNICAL FIELD

This invention relates to a system for the measurement of the radius of the cornea of an eye, and more particularly to the provision of a dual image formed to produce a parallel line offset-overlap pattern in measurement of the parameters related to cornea radius.

BACKGROUND ART

In ophthalmology, devices known as keratometers have been used to measure the curvature of radius of the cornea. One method is to measure an image size for a fixed object. In another approach, the image size is caused to be fixed by varying the size of the object viewed through a microscope after reflection from a cornea. Systems involving the use of the calibration on zoom lenses have also been employed in the keratometer art.

Difficulty has been encountered in various systems by reason of the fact that the human eye is not quiescent, but constantly moves back and forth, making difficult certain of the measurements involved.

DISCLOSURE OF THE INVENTION

In accordance with the present invention, a pair of linear parallel spaced apart objects are viewed as reflected from the cornea, the view being taken through a square rod of refractile transparent material mounted in the field of view of the microscope where a diagonal cross sectional plane of the rod is common to the optical axis of the microscope. Means are provided for rotating the rod about the optical axis of the microscope to produce a parallel line offset-overlap pattern of the objects as viewed through the rod. Means are then provided for measuring the angle between a perpendicular from the long axis of the objects and the axis of the rod at which angle the pattern is produced to provide data by which the radius of the cornea can be calculated.

DETAILED DESCRIPTION

Figure 1:
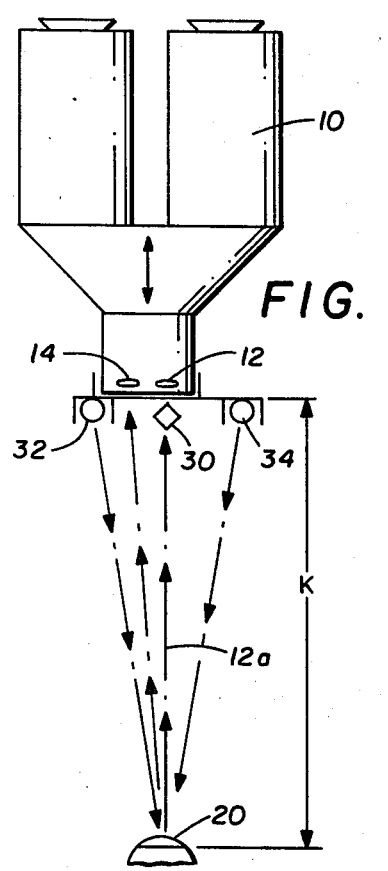
FIG. 1 is a schematic elevation view of a system embodying the present invention.

Referring now to FIG. 1, an ophthalmologist's microscope 10 is shown in position for viewing the cornea 20 of a patient. The microscope 10 is provided with dual paths which include an objective lens 12 in one path and an objective lens 14 in the other path. In accordance with the present invention, a rod 30 of transparent refractile material is employed together with a pair of objects or light sources 32 and 34. Rod 30 is shown as being square for illustrative purposes; however, a prism and for example, a double edge prism can also be utilized with the present invention. As used throughout the present description, the term rod shall include a prism structure. Sources 32 and 34 form a unique object pattern as viewed solely through lens 12 and rod 30.

Figure 2:
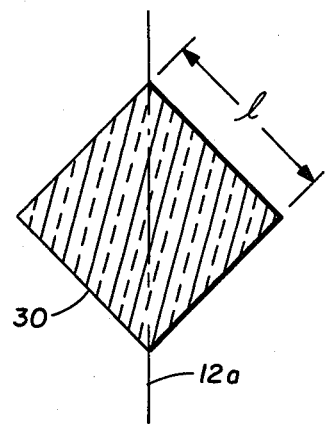
FIG. 2 is an enlarged view of the rod of FIG. 1.

The radius of the cornea 20 is to be determined in accordance with the geometrical relationships expressed in the following equation:

$$r = 2KI/O \qquad (1)$$

where:
- $r$ = the radius of cornea 20;
- $K$ = the focal length in the microscope objective lens (FIG. 1);
- $O$ = the separation between the light sources 32 and 34 (FIG. 3);
- $I = l \sin 45 \times \sin \alpha$ = Image produced by the cornea, where $\alpha$ (FIG. 3) is the angle between a perpendicular from the long axis of objects 32 and 34 and the axis of rod 30 at which the parallel line offset-overlap pattern is achieved, and $l$ is the length of the side of the rod 30 (FIG. 2).

The invention involves the use of the parallel sources 32 and 34. Rod 30 is mounted with its cross sectional diagonal coinciding with the axis 12a as shown in FIG. 2. Rod 30 is rotatable about the axis 12a in a plane parallel to the plane common to the axes of objects 32 and 34.

Figure 3:
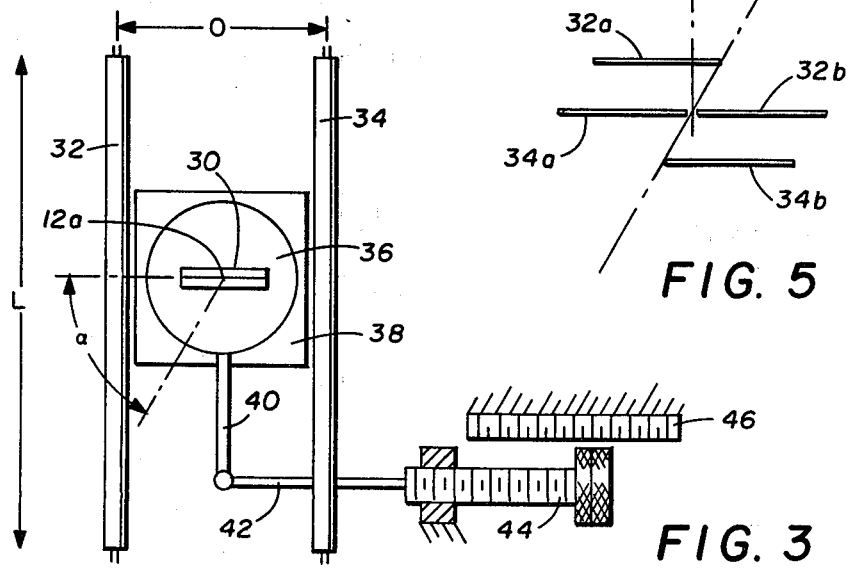
FIG. 3 is a bottom view of portions of the unit shown in FIG. 1 with the rod rotated 90° from the position shown in FIG. 1.

Referring to FIG. 3, objects 32 and 34 are light sources, in one form, elongated slim fluorescent lamps. By way of example, objects 32 and 34 may be of the order of 25 cm. in length and spaced apart a distance O of about 8.5 cm. (FIG. 3). Microscope 10 may have an objective lens 12 of focal length of about 17.5 cm. In FIG. 2, rod 30 has been shown enlarged with the cross sectional plane corresponding with the axis 12a. The rod 30 may have a length L of about 3 mm to about 7 mm depending on the size of the image to be measured.

In FIG. 3, the rod 30 is shown mounted on a rotatable disc 36 which is supported on a tray 38. Disc 36 may be rotated in a plane perpendicular to the axis 12a and in a plane parallel to the plane common to the axes of sources 32 and 34.

Disc 36 is provided with an actuating arm 40 which is coupled to a rod 42 which is driven by micrometer screw 44. Micrometer screw 44 may be employed in connection with a calibrated scale 46 to indicate the angle through which the rod 42 is actuated as the micrometer screw 44 is rotated.

Figure 4:
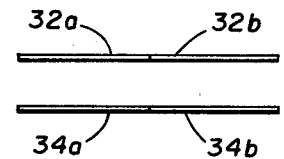
FIG. 4 illustrates a view of the pattern involved in the present measurement.

Referring now to FIG. 4, objects 32 and 34 appear as solid bars 32a and 34a when viewed through lens 12 of microscope 10 of FIG. 1 with the length of the rod 30 parallel to the lengths of the objects 32 and 34. However, as disc 36 is rotated, there will be one angle $\alpha$ at which the pattern of FIG. 4 is changed to the pattern shown in FIG. 5. The double image of sources 32 and 34, by reason of the view of the same through a square rod, is caused to form the parallel line offset-overlap pattern of FIG. 5. In such pattern, the object image bar 32b is parallel to and aligned with the image bar 34a with the bar 32a being offset to one side of the line 32b and 34a. Image bar 34b is offset to the other side. Once the angle α is determined, then all other elements of Equation (1) are known, except the radius r, and the radius r can then be readily calculated.

Having described the invention in terms of the schematic representations and diagrams of FIGS. 1–5, there will now be presented a description of a preferred embodiment of the invention.

Figure 6:
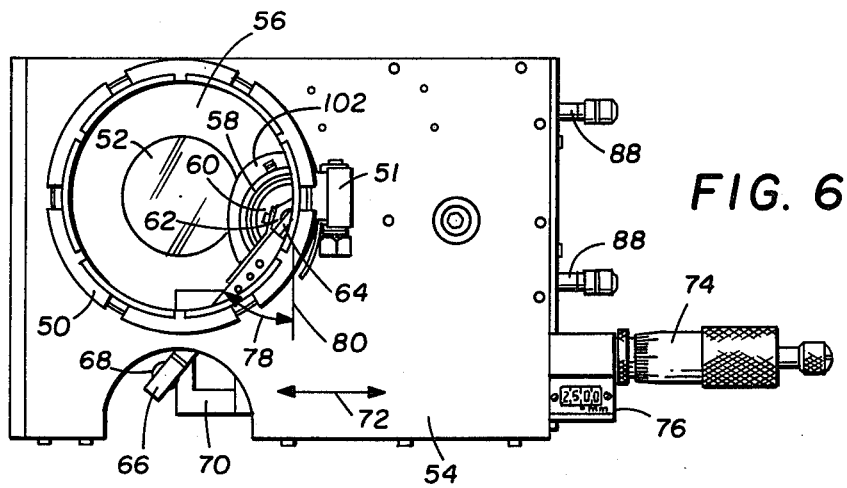
FIG. 6 is a top view of an embodiment of the invention adapted to be secured to the housing of objective lenses of a microscope normally used in eye examination treatment procedures.

Referring to FIG. 6, a cylindrical adaptor 50 is provided in a configuration suitable to be clamped as by a screw clamp 51 to the housing of a microscope objective lens. By this means, objective lenses, such as lenses 12 and 14, FIG. 1, on the microscope will be positioned to view objects through a transparent disc 52 which may contain a filter lens. In the following description, it will be presumed that the axis of the microscope will be in a vertical position so that the disc 52 would be in a horizontal plane and so that adaptor 50 would be secured to vertical cylindrical portions of the microscope object housing. In such configuration, a main frame comprising a flat horizontal mounting plate 54 is secured to the lower end of adaptor 50. Thus, when adaptor 50 is secured to the microscope, it will remain in a fixed position relative to the microscope. The plate 54 is also fixed, immovable related to adaptor 50.

Mounting plate 54 slidably and rotatably supports a subframe 56 comprising a lower tray or panel, a portion of which is seen through adaptor 50. Disc 52 is mounted in subframe 56. In addition to disc 52, a fixture 58 is supported from subframe 56 beneath plate 54. A bearing 60 supported from subframe 56 serves to mount a fixture 62 which is rotatable in bearing 60 relative to subframe 56. Bearing 60 serves to support a rod 64. Rod 64 corresponds to the rod 30 shown in FIG. 1 and may comprise, for example, a prism.

An arm 66 is secured to and extends from the fixture 62 which supports the rod 64. Arm 66 is provided with a contact roller 68 and is normally biased by a spring (not shown in FIG. 6) in a counter-clockwise direction. Roller 68 bears against the end of a travelling bar 70. Bar 70 may be manually adjusted for movement in the direction of arrow 72 by the action of a micrometer screw 74. A counter 76 is geared to the micrometer screw 74 so that a suitable reading can be obtained from counter 76 indicating the number of revolutions of the micrometer screw 74. This, in turn, is calibrated in terms of the angle 78 that the rod 64 makes relative to a line 80 which is perpendicular to the length or the long dimension of subframe 56.

Figure 7:
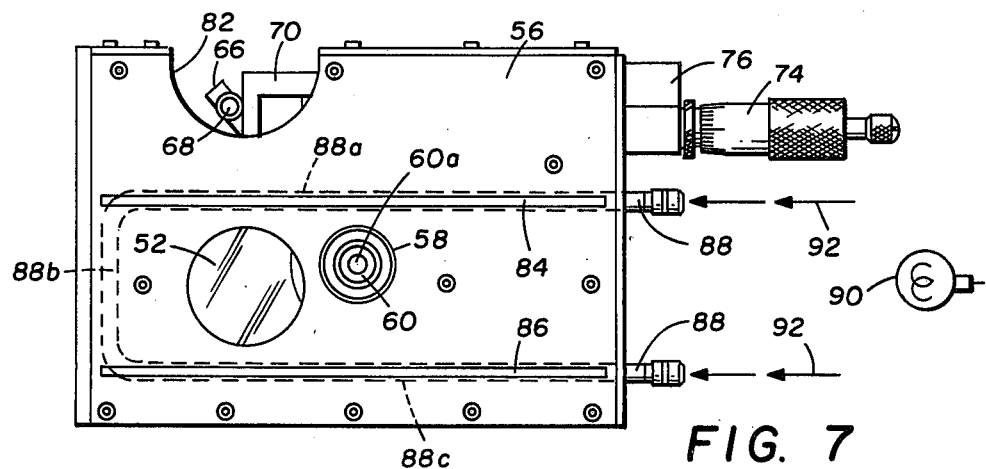
FIG. 7 is a bottom view of the unit of FIG. 6.

As best seen in FIG. 7, a bottom view of the unit of FIG. 6, the lower panel of subframe 56 has an arcuate portion 82 cutaway in the region of the arm 66 and the bar 70. Fixture 58 can be seen through an opening in the bottom of subframe 56. The bearing unit 60 is also visible from the bottom. A clear aperture 60a extends through the center of the bearing 60 to accommodate a view of the object beneath the microscope through the aperture 60a.

A pair of slots 84 and 86 extend the length of the bottom panel of subframe 56. They are long, narrow slits and are parallel to each other and perpendicular to line 80, FIG. 6. Slot 84 is closer to the center of aperture 60a than slot 86. A light pipe 88 extends from a point adjacent micrometer screw 74 along the length of subframe 56 immediately above slot 84, namely portion 88a. A portion 88b extends laterally from portion 88a and a third longitudinal portion 88c. The portion 88c lies immediately above the slot 86.

Figure 8:
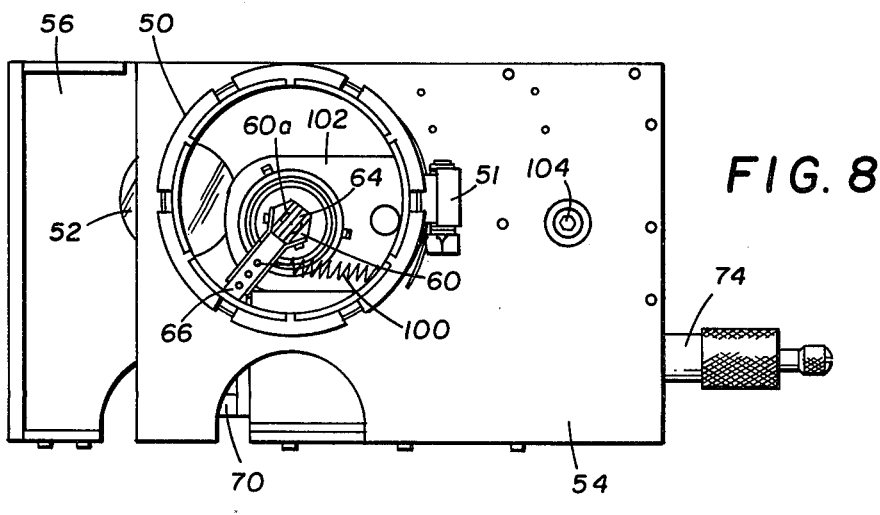
FIG. 8 is a top view of the system of FIG. 6 with the keratometer components moved into position for use thereof.

While not an integral part of the fixture of FIGS. 6–8, a light source 90 is provided for projecting a beam of light 92 along the end of the light pipe 88 so that the portions of the light pipe 88 viewed through slots 84 and 86 corresponds to the light sources 32 and 34 of FIG. 3.

As shown in FIG. 8, subframe 56 and the structure it supports has been slidably displaced to the left relative to the axis of the adaptor 50 so that the bearing 60 carrying the rod 64 is centered under an objective lens such as objective lens 12 of FIG. 1. In this position, the second objective lens is blocked out so that the only view the operator of the microscope has is through the aperture 60a by way of the rod 64.

In FIG. 8, it will be noted that a spring 100 is coupled to arm 66 to bias arm 66 counter-clockwise so that the roller 68 of FIGS. 6 and 7 will maintain with the bar 70.

Figure 5:
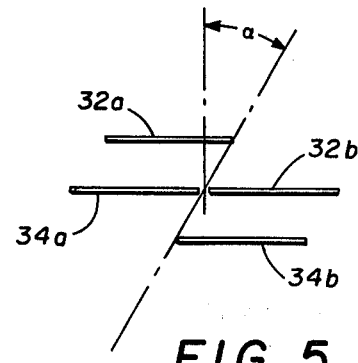
FIG. 5 illustrates a parallel line offset-overlap pattern of the pattern of FIG. 4.

With the structure thus far described in connection with FIGS. 6–8, the unit is to be clamped onto a microscope. When its use as a keratometer is required, it will be displaced from the portion shown in FIGS. 1 and 2 to the position shown in FIG. 8 wherein a median point on rod 64 is at the axis of one of the two objective lenses. In this position, the two elongated lighted slots 84 and 86 will appear to the viewer through the rod 64. The micrometer-type adjusting screw 74 will then be rotated to change the angle 78 at which the axis of the rod 64 makes relative to line 80, FIG. 6. The adjustment is made until the pattern illustrated in FIG. 5 is viewed through the rod 64. At this point, the counter 76 may be read and the reading utilized in connection with Equation (1) to determine the curvature of the cornea.

In FIG. 8, a flat thin bar 102 is provided on which the fixture 58 is mounted. The flat bar 102 is supported by bolts 104 to the plate 54. It is by use of the bar 102 that the lower panel and all the apparatus supported thereon can be rotated relative to the plate 54 and into the position illustrated in FIG. 9. Rotation through ninety degrees permits measurement of curvature of an eye along two mutually perpendicular planes as well as at intermediate angles if desired.

Figure 9:
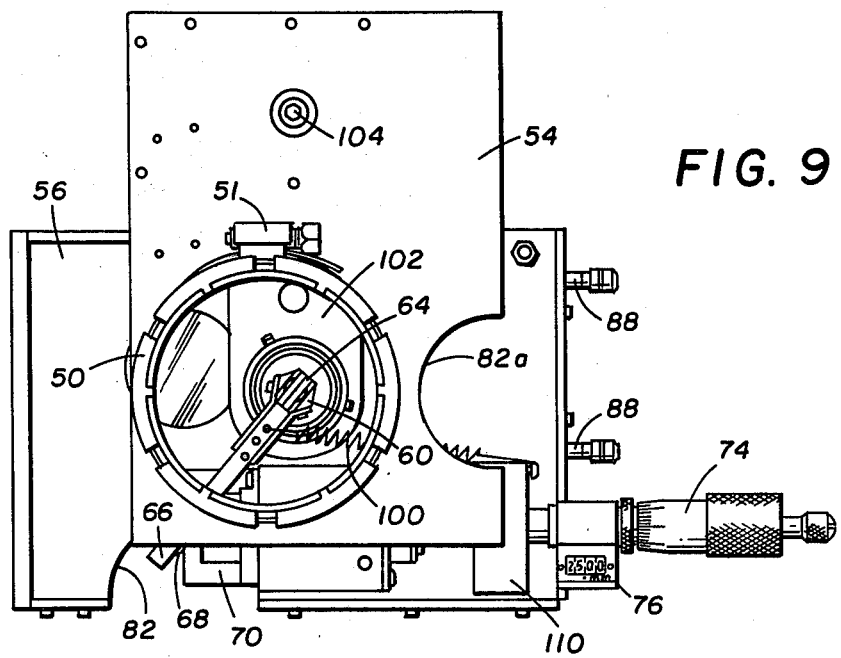
FIG. 9 is a top view of the keratometer in the same operative position, but rotated 90° relative to the microscope mounting.

Thus, in the position shown in FIG. 9, ninety degrees from the position shown in FIG. 8, and at other angles, the curvature of the cornea can be obtained relative to any axis with respect to the axis of measurement at the position shown in FIGS. 6–8.

Figure 10:
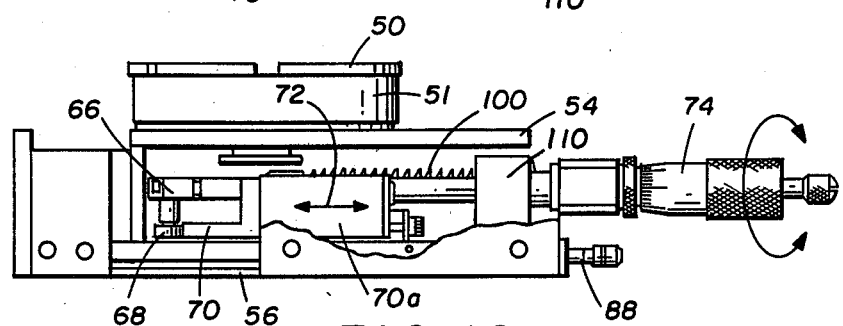
FIG. 10 is a side view, partially broken away of the unit of FIG. 6.
Figure 11:
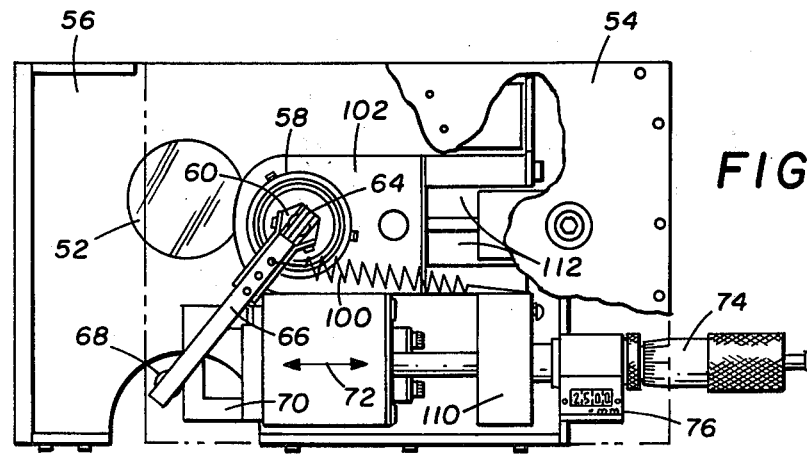
FIG. 11 is a top view of the unit of FIG. 8 with the top panel partially broken away.

As best shown in FIGS. 10 and 11, the micrometer screw 74 is mounted in a block 110 which is secured to the subframe 56 so that as the micrometer screw 74 is rotated, a slide unit 70a moves in accordance with arrow 72 and carries the bar 70 to move arm 66 through action of the roller 68 which is mounted on a short shaft depending from arm 66. The mounting bar 102 is secured through slide structure 112 (FIG. 11) which in turn is secured to the upper panel 64 so that the bar 102 is supported by the plate 54 and in turn supports the lower panel 56 so that the lower panel 56 can move between the positions shown in FIGS. 6 and 8 and can rotate between the positions shown in FIGS. 8 and 9.

When the keratometer portions of the system are not in use, such portions of the system will occupy positions shown in FIG. 6 so that the usual unimpeded use of the microscope can proceed. The keratometer elements are readily available and may simply be brought into position by sliding from the position shown in FIG. 6 to the positions shown in FIGS. 8 and 9.

Having described the invention in connection with certain specific embodiments thereof, it is to be understood that further modifications may now suggest themselves to those skilled in the art, and it is intended to cover such modifications as fall within the scope of the appended claims.

I claim:

1. In an optical instrument employing a microscope adapted to bring into focus the cornea of a patient's eye to provide a reference distance in connection with the measurement of the radius of curvature of said cornea, the combination which comprises:
   (a) a pair of parallel spaced apart linear objects in a plane perpendicular to the optical axis of the eye and of said microscope;
   (b) a rod of refractile transparent material mounted in the field of view of said microscope with a diagonal of the cross-section thereof common to the optical axis of said microscope;
   (c) means for rotating said rod around the optical axis of said microscope to produce a parallel line offset-overlap pattern of said objects as viewed through said rod; and
   (d) means for measuring the angle between:
      (i) a perpendicular from the long axes of said objects; and
      (ii) the orientation of said rod at which said pattern is produced.

2. The combination set forth in claim 1 in which said objects comprise a pair of linear spaced apart parallel luminous bodies.

3. The combination set forth in claim 1 in which said pair of objects and said rod are both rotatable around the axis of said microscope through an angle of ninety degrees for measurement of said curvature along mutually perpendicular planes.

4. In an optical instrument employing a microscope adapted to bring into focus the cornea of a patient's eye in connection with the measurement of the radius of curvature of said cornea, the combination which comprises:
   (a) a main frame including mounting structure for securing said main frame to a microscope;
   (b) a subframe slidably mounted on said main frame for movement perpendicular to the axis of said microscope;
   (c) a pair of parallel spaced apart linear objects mounted on the bottom of said subframe and lying in a plane perpendicular to the optical axis of the eye and of said microscope;
   (d) a rod of refractile transparent material mounted on said subframe and movable by slide movement of said subframe into and out of the field of view of said microscope, said rod being segmented when in said field of view with a diagonal of the cross-section thereof common to the optical axis of said microscope;
   (e) means for rotating said rod relative to said subframe around the optical axis of said microscope to produce a parallel line offset-overlap pattern of said objects as viewed through said rod; and
   (f) means for measuring the angle between:
      (i) a perpendicular from the long axes of said objects; and
      (ii) the orientation of said rod at which said pattern is produced.

5. The combination set forth in claim 4 in which said subframe is rotatable relative to said main frame through an angle of ninety degrees for measurement of said curvature along two mutually perpendicular planes.

6. In an optical instrument employing a microscope adapted to bring into focus the cornea of a patient's eye to provide a reference distance in connection with the measurement of the radius of curvature of said cornea, the combination which comprises:
   (a) a pair of parallel spaced apart light emitting tubes lying in a plane perpendicular to the optical axis of the eye and of said microscope and located on opposite sides of said axis;
   (b) a square rod of refractile transparent material mounted in the field of view of said microscope with a medial diagonal of the cross-section thereof common to the optical axis of said microscope;
   (c) means for rotating said rod around the optical axis of said microscope to produce a parallel line offset-overlap pattern of said objects as viewed through said rod; and
   (d) means for measuring the angle between:
      (i) a perpendicular from the long axes of said objects; and
      (ii) the orientation of said rod at which said pattern is produced.

7. The combination set forth in claim 6 wherein mounting structure for said rod includes an arm rotatable about the axis of said microscope carrying said rod with unimpeded view of said eye through said rod and with angle measuring follower means associated with said arm for sensing said angle.

8. In measurement of the curvature of the cornea of an eye the method comprising:
   (a) establishing an object pattern comprising a pair of parallel spaced apart linear objects positioned for reflection from said cornea;
   (b) viewing the reflection of said pattern through a refractile transparent rod at a reference position where a medial diagonal of said rod is located at the line of sight of said pattern and whose length dimension is perpendicular to the length of said objects;
   (c) rotating said rod about said line of sight from said reference position through an angle to a new position at which said pattern viewed through said rod appears as a parallel line offset-overlap pattern; and
   (d) measuring said angle to provide for calculation of said curvature.

* * * * *